(12) United States Patent
Jeong et al.

(10) Patent No.: US 8,911,706 B2
(45) Date of Patent: Dec. 16, 2014

(54) COMPLEX OF BIFUNCTIONAL CHELATING AGENT AND MANNOSYL HUMAN SERUM ALBUMIN

(75) Inventors: Jae Min Jeong, Seoul (KR); Myung Chul Lee, Seoul (KR); June Key Chung, Seoul (KR); Dong Soo Lee, Seoul (KR)

(73) Assignee: SNU R&DB Foundation (KR)

( * ) Notice: Subject to any disclaimer, the term of this patent is extended or adjusted under 35 U.S.C. 154(b) by 323 days.

(21) Appl. No.: 13/146,280

(22) PCT Filed: Jan. 27, 2010

(86) PCT No.: PCT/KR2010/000488
§ 371 (c)(1),
(2), (4) Date: Aug. 10, 2011

(87) PCT Pub. No.: WO2010/087612
PCT Pub. Date: Aug. 5, 2010

(65) Prior Publication Data
US 2011/0286920 A1    Nov. 24, 2011

(30) Foreign Application Priority Data
Jan. 28, 2009  (KR) .................. 10-2009-0006553

(51) Int. Cl.
| A61K 51/00 | (2006.01) |
| A61K 36/14 | (2006.01) |
| A61K 51/08 | (2006.01) |
| A61K 51/04 | (2006.01) |

(52) U.S. Cl.
CPC ........... *A61K 51/081* (2013.01); *A61K 51/0482* (2013.01)
USPC ....................................... 424/1.11; 424/1.65

(58) Field of Classification Search
CPC ................. A61K 51/0482; A61K 51/081
USPC .................................................. 424/1.11
See application file for complete search history.

(56) References Cited

U.S. PATENT DOCUMENTS 4,634,586 A * 1/1987 Goodwin et al. ............. 424/1.65
7,563,433 B2 * 7/2009 McBride et al. ............. 424/1.89

FOREIGN PATENT DOCUMENTS

| KR | 20030026153 A | 3/2003 |
| KR | 100557008 B1 | 3/2006 |

OTHER PUBLICATIONS

Deal et al. (Nucl. Med. Biol. 1998, 25, 379-385).*
Hoffend et al. (Nucl. Med. Biol. 2005, 32, 287-292).*
McCurry, Thomas J. et al., Synthesis of 2-(p-Thiocyanatobenzyl-1,4,7-triazacyclononane-1,4,7-triacetic Acid: Application of the 4-Methoxy-2,3,6-trimethylbenzenesulfonamide Protecting Group of the Synthesis of Macrocyclic Polyamines, Bioconjugate Chem., 1993, 4, pp. 236-245.
Deal, Kim A. et al., Evaluation of the Stability and Animal Biodistribution of Gadolinium(III) Benzylamine-Derivatized Diethylenetriaminepentaacetic Acid, J. Med. Chem, 1996, 39, pp. 3096-3106.
Stahl, Philip, et al., Receptor-Mediated Pinocytosis of Mannose Glycoconjugates by Macrophages: Characterization and Evidence for Receptor Recycling, Jan. 1980, Cell, vol. 19, pp. 207-215.
Mariani, Giuliano, et al., Radioguided Sentinel Lymph Node Biopsy in Breast Cancer Surgery, The Journal of Nuclear Medicine, Aug. 2001, vol. 42, No. 8, pp. 1198-1215.
Mariani, Giuliano, et al., Radioguided Sentinel Lymph Node Biopsy in Malignant Cutaneous Melanoma, Sentinel Node Biopsy in Melanoma, J. Nuclear Medicine, 2002, 43, pp. 811-827.
Phillips, William T., et al., Evaluation of [99mTc] liposomes as lymphoscintigraphic agents: comparison with [99mTc] sulfur colloid and [99mTc] human serum albumin, Nuclear Medicine and Biology, 2001, 28, pp. 435-444.
Jeong, Jae Min, et al., Development of 99mTc-neomannosyl human serum albumin (99mTc-MSA) as a novel receptor binding agent for sentinel lymph node imaging, Nuclear Medicine Communications, 2004, 25, pp. 1211-1217.

* cited by examiner

*Primary Examiner* — Michael G Hartley
*Assistant Examiner* — Melissa Perreira
(74) *Attorney, Agent, or Firm* — Heslin Rothenberg Farley & Mesiti P.C.

(57) ABSTRACT

The present invention is about bifunctional chelating agents (BCA) conjugated mannosyl human serum albumin (MSA) and its radioisotope labeled compounds for imaging immune system such as macrophages, Kupffer cells, reticuloendothelial system (RES), and lymphatic system. The present invention comprises BCA-MSA conjugates, their radiolabeled compounds, and kits for radiolabeing. The present invention improved radiolabeling procedure, showed higher lymphatic system uptake, and enabled image by positron emission tomography (PET).

1 Claim, 5 Drawing Sheets

COMPLEX OF BIFUNCTIONAL CHELATING AGENT AND MANNOSYL HUMAN SERUM ALBUMIN

CROSS REFERENCE TO RELATED APPLICATION

This application is the National Phase filing of International Application No. PCT/KR2010/000488, filed Jan. 27, 2010, which claims priority to Korean Application No. 10-2009-0006553, filed Jan. 28, 2009. The entire content of each prior application is hereby incorporated by reference.

TECHNICAL FIELD

The present invention relates to novel radiopharmaceuticals for imaging immune cells or tissues composed of immune cells such as macrophages, Kupffer cells, reticuloendothelial system (RES), and lymphatic system.

BACKGROUND ART

Lymphatic system imaging is important for diagnosis of lymph nodes in nuclear medicine. In cases of breast cancer and melanoma, excessive excision can be avoided during surgery if sentinel lymph node, the closest lymph node to the tumor tissue, can be detected by injecting radiocolloid into the tumor. The detected sentinel nodes are subject to biopsy to detect metastases of which presence would affect the decision making for excision. This is very important for after-surgery adverse reaction and cosmetic. (G. Mariani, L. Moresco, G. Viale, G. Villa, M. Bagnasco, G. Canavese, J. Buscombe, H. W. Strauss, G. Paganelli. "Radioguided sentinel lymph node biopsy in breast cancer surgery." J. Nucl. Med. 2001; 42:1198-1215; G. Mariani, M. Gipponi, L. Moresco, G. Villa, M. Bartolomei, G. Mazzarol, M. C. Bagnara, A. Romanini, F. Cafiero, G. Paganelli, H. W. Strauss. "Radioguided sentinel lymph node biopsy in malignant cutaneous melanoma" J. Nucl. Med. 2002; 43:811-827)

Lymph nodes can be imaged using an adequate radiocolloid which is injected into tissue and is successively moved and trapped into lymph nodes. The lymph node in which radioactivity is accumulated can be detected by a gamma probe. Most of the radiopharmaceuticals used for imaging and detection of lymph nodes are $^{99m}$Tc labeled colloids such as antimony sulfur colloid (10~20 nm), albumin nano colloid (50 nm), and sulfur colloid (100~200 nm). The colloids with smaller particle size are more ideal because of rapid lymph node uptake. Antimony sulfur colloid is the best agent among currently used colloids because of the smallest particle size. However, its particle size is still too big and it requires 2 hr boiling time for labeling which is not adequate for the patients who should go to surgery in the early morning. In addition, it can become unstable after neutralization, which is prepared in strong acid medium.

To solve the problems, $^{99m}$Tc-human serum albumin (HSA) has been used, which has particle size of 6~8 nm. $^{99m}$Tc-HSA can be labeled rapidly and shows rapid movement to lymph nodes. However, it shows low contrast lymph node images and uptakes not only in sentinel lymph nodes but also in other lymph nodes because it does not accumulate in but bypasses the lymph nodes. (W. T. Phillips, T. Andrews, H.-L. Liu, R. Klipper, A. J. Landry Jr, R. Blumhardt, B. Goins. "Evaluation of [$^{99m}$Tc] liposomes as lymphoscintigraphic agents: comparison with [$^{99m}$Tc] sulfur colloid and [$^{99m}$Tc] human serum albumin" Nucl. Med. Biol. 2001; 28:435-444)

To solve the problem, a new radiopharmaceutical, so called disulfide reduced mannosylated human serum albumin (MSA), which can strongly binds with mannose receptors existing on immune cells, is easy to label with $^{99m}$Tc, has adequate molecular size to be absorbed to lymph capillary, and has no adverse reaction to human body, was developed. (Korean Patent 10-0557008, Disulfide reduced mannosylated serum albumin for lymphoscintigraphy and radiolabeled compounds comprising it. Feb. 23, 2006; Jeong J M, Hong M K, Kim Y J, Lee J, Kang J H, Lee D S, Chung J K, Lee M C. Development of $^{99m}$Tc-neomannosyl human serum albumin ($^{99m}$Tc-MSA) as a novel receptor binding agent for sentinel lymph node imaging. Nucl Med Commun. 2004 25(12):1211-7) It is known that MSA can strongly bind with mannose receptor (P. Stahl. Et al, Cell 1980; 19:207~215). So in the above patent, it was postulated that the lymph nodes can be imaged if MSA is labeled with an adequate radionuclide for imaging such as $^{99m}$Tc. Furthermore, MSA would show more rapid lymph node uptake because of its small size 6~8 nm. However, MSA itself cannot be labeled with $^{99m}$Tc without modification. So, disulfide reduced MSA was prepared by treating it with adequate reducing agents such as β-mercaptoethanol and dithiothreitol. There is a report that disulfide reduced galactosylated or lactosylated human serum albumin is labeled with $^{99m}$Tc after reducing disulfide bonds by treating with reducing agents. (Korean Patent 0464917. New disulfide reduced galactosylated serum albumin thereof; a liver function imaging composition; and a radiolabeled compound comprising it. Dec. 24, 2004) However, these $^{99m}$Tc-labeled agents cannot be imaged by positron emission tomography (PET).

Recently, the need for positron labeled radiopharmaceuticals for immune cell imaging increased, because PET is widely spread due to its superiority to conventional gamma images, and furthermore, positron or beta probes for detecting metastases are developed. Generally, positron emitters such as and $^{18}$F, $^{11}$C, $^{13}$N, and $^{15}$O are produced by cyclotron. Among these, only $^{18}$F is applicable for lymph node imaging because of its relatively long half-life (110 min) compare to other radionuclides. However, its labeling procedure requires evaporation and heating at high temperature, those are complicate and causes of protein denaturation. Moreover, production of $^{18}$F requires expensive cyclotron system.

DISCLOSURE OF THE INVENTION

The objects of the present invention are to develop conjugates of bifunctional chelating agent (BCA) and MSA, their radiolabeled compounds, and preparation of kits for radiolabeling. And thus the expected effects are convenient labeling with positron emitter $^{68}$Ga, high stability of the labeled compounds, and excellent immune system imaging including lymph nodes due to high accumulation in the lymph nodes, liver, and spleen.

The candidate BCAs forming stable complexes with $^{68}$Ga are 1,4,7-triazacyclononane-1,4,7-triacetic acid (NOTA) and 1,4,7,10-tetraazacyclododecane-1,4,7,10-tetraacetic acid (DOTA), and NOTA is more preferable between these two.

The selected radionuclide for labeling the MSA and BCA conjugates to detect and image immune cells is $^{68}$Ga.

Another object of this invention is to provide a kit that can make the radiopharmaceutical preparation for detecting and imaging immune cells easily. In detail, the object of the invention is to provide a pharmaceutically compatible kit for imaging immune cells which is composed of BCA-MSA and buffer solution in sterile vial and easily can be labeled with metallic radionuclides.

The present invention relates to,
(1) A conjugate of bifunctional chelating agent (BCA) and mannosyl human serum albumin (MSA) represented by following Formula 1:

[Formula 1]

wherein, Man is mannosyl group;
$L_1$ and $L_2$ are independently linker(s) or direct conjugation(s);
A is human serum albumin;
BCA is bifunctional chelating agent selected from 1,4,7-triazacyclononane-1,4,7-triacetic acid (NOTA) or 1,4,7,10-tetraazacyclododecane-1,4,7,10-tetraacetic acid (DOTA); and
m and n are independently integers from 1 to 58;
(2) The conjugate of (1), wherein $L_1$ and $L_2$ are independently direct conjugation(s) or (a) linker(s) comprising one or more residues selected from the group consisting of $C_1$~$C_{10}$ alkyl, $C_4$~$C_{10}$ aryl, thiourea, triazole, monopeptide, dipeptide, tripeptide, $C_4$~$C_{10}$ cycloalkyl, benzyl, thioether, amine, amide, ester, thioester, ether, hydrazine, hydrazide, pentosyl, and hexosyl;
(3) The conjugate of (1), wherein $L_1$ and $L_2$ are independently selected from the following formula:

wherein, Man is mannosyl group; and HSA is human serum albumin;
(4) The conjugate of (1), wherein $C_1$ carbon of mannose is conjugated with albumin or linker;
(5) A composition comprising the conjugate of bifunctional chelating agent (BCA) and mannosyl human serum albumin (MSA) of the above (1) or (2) labeled with a metallic radioisotope for imaging immune system;
(6) A composition of (5), wherein immune system is lymphatic system or reticuloendothelial system;.
(7) A composition of (5), wherein a metallic radioisotope is selected from the group consisting of $^{67}$Ga, $^{68}$Ga, $^{111}$In, $^{99m}$Tc, $^{186}$Re, $^{60}$Cu, $^{61}$Cu, $^{62}$Cu, $^{64}$Cu, $^{67}$Cu, $^{212}$Pb, $^{212}$Bi, and $^{109}$Pd;
(8) A composition of (5), wherein a metallic radioisotope is $^{68}$Ga;
(9) A sterile and apyrogenic kit of liquid, frozen or lyophilized state comprising 10 ng~100 mg of conjugate of (1) for preparation of a pharmaceutical composition labeled with a metallic radioisotope;
(10) A kit of (9) further comprising 0.01 mL~10 mL of 1 μM~10 M buffer (pH 1~9);
(11) A kit of (10), wherein the buffer solution is a mixture of acids selected from the group consisting of acetic acid, phosphoric acid, citric acid, fumaric acid, lactic acid, succinic acid, tartaric acid, carbonic acid, glucoheptonic acid, gluconic acid, glucuronic acid, glucaric acid and boric acid, and sodium or potassium salt thereof.
In the present invention, BCA-MSA derivatives, their radiolabeled compounds, and their radiolabeling kits show easier radiolabeling with metallic positron emitters such as $^{68}$Ga, show higher stability, and show better characteristics for lymphatic system imaging due to high lymphatic system accumulation compare to the conventional radiolabeled agents for imaging and detection of immune system.

The present invention relates to BCA-MSA conjugates represented by following Formula 1:

[Formula 1]

wherein, Man is mannosyl group;
$L_1$ and $L_2$ are indipently linker(s) or direct conjugation(s);
A is human serum albumin;
BCA is bifunctional chelating agent selected from 1,4,7-triazacyclononane-1,4,7-triacetic acid (NOTA) or 1,4,7,10-tetraazacyclododecane-1,4,7,10-tetraacetic acid (DOTA); and
m and n are independently integers from 1 to 58.

The above human serum albumin is composed of a single polypeptide protein which has molecular weight of 66,462, long axis is 8 nm, short axis is 6 nm, isoelectric point is 4.8, and composes about 50% of serum protein. It contains 59 amino residues comprising 58 lysine and one N-terminal. Thus the maximum BCA and mannose binding to amino groups can be 59 in total.

The above BCA-MSA solution is more stable at frozen state. However, it would be stable at refrigeration, if it is freeze-dried. The freeze-dried product might be more stable under oxygen-free or vacuum condition.

When BCA or mannose conjugate with human serum albumin in the present invention, they can be directly conjugated or conjugated via linkers. Linker or human serum albumin can be conjugated with any $C_1$~$C_6$ position of mannose. Mannose ring can be opened if $C_5$ is conjugated. Furthermore, α- or β-conjugations are included in $C_1$ position. Although only β-$C_1$-conjugation is shown in the Examples, the present invention includes all the above described conjugations. Above linkers $L_1$ or $L_2$ can be one or more residues selected from $C_1$~$C_{10}$ alkyl, $C_4$~$C_{10}$ aryl, thiourea, triazole, monopeptide, dipeptide, tripeptide, $C_4$~$C_{10}$ cycloalkyl, benzyl, thioether, amine, amide, ester, thioester, ether, hydrazine, hydrazide, pentosyl, and hexosyl.

The preferable $L_1$ and $L_2$ are shown as the following formulas:

wherein, Man is mannosyl group; and HSA is human serum albumin.

The above mannosyl and mannosyl group comprising linker(s) conjugate with amino group of serum albumin. For example, serum albumins conjugated with mannose directly or via linker(s) are as following formulas 2 and 3. As needed, the said mannosyl human serum albumin may comprise 1~58 mannoses or mannoses containing linker(s).

[Formula 2]

-continued

[Formula 3]

Formula 2 shows directly conjugated mannose and human serum albumin, and Formula 3 shows mannose and human serum albumin conjugated via phenyl group as a linker. The above MSAs in Formula 2 or Formula 3 are conjugated with BCAs such as NOTA or DOTA.

The presence invention comprises the preparation method of BCA-MSA conjugates in Formula 1. In detail, it comprises step of conjugating mannose with human serum albumin directly or via linkers to make MSA (step 1), and step of conjugating BCA such as NOTA or DOTA with MSA directly or via linkers (step 2), in which the order of Step 1 and 2 can be reversed.

Step 1 comprises chemical modification of mannose or its linker to have function group such as thiocyanate, ester, aldehyde or iminomethoxyalkyl to enable them to conjugate with human serum albumin and conjugation with human serum albumin. In detail, Scheme 1 shows the preparation method of MSA in Formula 2 using 2-imino-2-methoxyethyl-1-thio-β-D-mannose (IME-thiomannose).

D-mannose is acetylated, brominated, conjugated with thiourea, and reacted with chloroacetonitrile to give cyanomethyl 2,3,4,6-tetra-O-acetyl-1-thio-β-D-mannopyranoside. The product is reacted with sodium methoxide in the methanol solution to give IME-thiomannose. MSA is synthesized by reacting human serum albumin with IME-thiomannose at pH 8~9 to form thiocarbamyl bond (Scheme 1).

Phenylmannosyl human serum represented by Formula 3 is synthesized according to Scheme 2.

[Scheme 2]

As shown in the above scheme 2, isothiocyanate at the end of the phenyl group of phenylmannose conjugates with amino group of human serum albumin to give phenyl mannosyl human serum albumin of Formula 3.

Step 2 comprises conjugation of MSA and BCA such as NOTA or DOTA. For this, carboxyl group of NOTA or DOTA is conjugated with amino group of MSA by formation of amide bond (Scheme 3), or NOTA or DOTA derivatives containing isothiocyanatobenzyl group is conjugated with amino group of MSA by formation of thiourea (Scheme 4), and so on.

[Scheme 3]

[Scheme 4]

The present invention comprises the radiolabeled BCA-MSA of Formula 1.

The above radiosotopes comprise $^{67}Ga$, $^{68}Ga$, $^{111}In$, $^{99m}Tc$, $^{188}Re$, $^{186}Re$, $^{60}Cu$, $^{61}Cu$, $^{62}Cu$, $^{67}Cu$, $^{64}Cu$, $212Pb$, $^{212}Bi$, and $^{109}Pd$, more preferably comprise $^{68}Ga$ and $^{111}In$, and the most preferable one is $^{68}Ga$.

$^{68}Ga$ is a positron emitter produced from a generator and can be labeled to proteins in high yield via BCA. Furthermore, it is ideal for lymph node imaging and detection during surgery by positron probe because of 68 min half-life.

The above labeled compounds are prepared by addition of a radioisotope to BCA-MSA of Formula 1. The preparation is done under sterile and apyrogenic condition for direct human injection just after preparation.

The above prepared compounds can be administered into human body via subcutaneous injection, accumulates in the lymphatic system, can be imaged by PET scanner, and can be detected by a gamma or beta probe for lymph node metastases confirmation. If the above agent is administered via intravenous injection, it will show liver Kupffer cell or bone marrow macrophage image.

Furthermore, the present invention comprises pharmaceutically compatible apyrogenic and sterile kits containing 10 ng~100 mg of BCA-MSA represented by formula 1 for preparation of radiopharmaceuticals by labeling with metallic radioisotopes. Each kit also can contain 0.01~10 mL of buffer solutions (pH 1~9, 1 μM~10 M). The kits can be stored as solutions, frozen solutions or lyophilized powders.

Buffer solutions for the above kits are the mixture of acids selected from the group consisting of acetate, phosphate, citrate, fumarate, lactate, succinate, tartarate, carbonate, glucoheptonate, gluconate, glucuronate, glucarate and borate, and sodium or potassium salts thereof.

The above kits can contain additional antioxidants such as ascorbic acid and gentisic acid for prevention of radiolysis after radiolabeling. The recommended amount of antioxidants is 0~500 mg per dose.

The above kits can be frozen or freeze-dried in the presence of inactive gas. The above kits can contain vials containing sterile buffer solution, normal saline, syringes, filters, columns, and so on for convenient preparation of radiopharmaceuticals. It is well known to general workers in this field that such kits can be modified and transformed by personal requirements or diet requirements of patients, or by provision of radioisotopes.

The above kits are added with 0.1~500 mCi radionuclide per kit (per BCA-MSA 1 mg) and incubated for 0.1~30 min for preparation of radiopharmaceuticals. For example, $^{68}Ga$-NOTA-MSA could be successfully prepared with 98~100% efficiency after addition of generator eluted $^{68}GaCl_3$ into the kit for immune cell imaging and detection, and successive incubation at 37° C. for 1~30 min.

The Examples of the present invention confirmed that $^{68}Ga$-BCA-MSA was obtained with >95% efficiency, which was stable for 2 hr in 37° C. serum, and showed more rapid movement to inguinal lymph node after injection into mouse footpad.

BRIEF EXPLANATION OF DRAWINGS

FIG. 1. Diagram of BCA-MSA of the present invention. Mannoses and BCAs are conjugated directly or indirectly to human serum albumin.

Man: mannosyl group, $L_1$ and $L_2$: direct conjugation or linker.

EXAMPLES

The following examples are given to illustrate the present invention. It should be understood, however, that the invention is not to be limited to the specific conditions or details described in these examples.

Example 1

Preparation of Benzyl NOTA-thiomannosyl Human Serum Albumin

Step 1. Preparation of Mannosyl Human Serum Albumin (Scheme 1)

100 g of D-mannose was added slowly for 30 min to the mixture of 400 mL of acetic anhydride and 3 mL of perchloric acid with stirring. 30 g of amorphous phosphor was added to the reaction mixture and the container was cooled down with ice. 180 g of bromine was added slowly with keeping the temperature of the mixture below 20° C. and 36 mL of distilled water was slowly added for 30 min to prevent temperature rise. The reaction was proceeded for 2 hr after capping. 300 mL chloroform was added to the mixture and transferred into a separating funnel containing 800 mL ice water. Chloroform layer was pooled, phosphor was removed by filtration and the filtrate was washed with ice water twice. The chloroform layer was washed with sodium bicarbonate solution to remove residual acid, dehydrated with calcium chloride, evaporated under reduced pressure, dissolved in diethylether, recrystalized, and obtained as a crystal with mp 87° C. 9.74 g (20 mmol) of 2-S-(2,3,4,6-tetra-O-acetyl-β-D-mannopyranosyl)-2-thiopseudourea HBr was dissolved in 40 mL of water and acetone (1:1) mixture and 5 mL (79 mmol) of chloroacetonitrile was added to complete dissolve. 3.2 g (23.2 mmol) potassium carbonate and 4.0 g (40.4 mmol) sodium bisulfite was added and stirred for 30 min at room temperature. The reaction mixture was added to 160 mL ice water and stirred for 2 hr. The precipitate was collected by filtration and washed with cold water. The air dried precipitate was dissolved in boiling methanol and impurity was removed by filtration. Crystals were obtained from the filtrate after storing in a refrigerator (yield: 72%, mp: 95-97° C.). 40 mg of the recovered crystal was dissolved in 1.5 mL of anhydrous methanol at 40° C., 0.8 mg of sodium methoxide was added with stirring and reacted for 48 h at room temperature to give IME-thiomannose (22 mg, yield 55%). 22 mg of IME-thiomannose was added to 100 mg of human serum albumin in 1 mL of 0.2 M borate buffer (pH=8.5) with vigorous stirring. The mixture was reacted for 1.5 hr at 37° C. to give MSA and stored at −70° C. until use.

Step 2. Preparation of Benzyl-NOTA-thiomannosyl Human Serum Albumin 10 mg of p-SCN-Bz-NOTA was added to 1 mL of MSA (13.6 mg/mL) prepared by the above Step 1 reaction and reacted for 1 hr. Benzyl-NOTA-thiomannosyl human serum albumin was purified from the reaction mixture using a Sephadex G-25 column chromatography.

Example 2

Benzyl-NOTA-Phenyl Mannosyl Human Serum Albumin

Step 1. Preparation of Phenyl Mannosyl Human Serum Albumin (Scheme 3)

After dissolving 20 mg of human serum albumin in 5 mL of 0.1 M carbonate buffer (pH 9.5), 5.5 mg of α-L-mannopyranosylphenylisothiocyanate was added and reacted with stirring at room temperature for 20 hr. The resulting phenylmannosyl human serum albumin reaction mixture was stored in −70° C. until use.

Step 2. Preparation of Benzyl-NOTA-phenyl Mannosyl Human Serum Albumin 10 mg of p-SCN-Bz-NOTA was added to 1 mL of phenyl mannosyl human serum albumin prepared by Step 1 and reacted for 1 hr at room temperature. The resulting benzyl-NOTA-phenyl mannosyl human serum albumin was purified from the reaction mixture using a Sephadex G-25 column chromatography.

Example 3

Preparation of Kits for Immune Cell Imaging 1 mL of benzyl-NOTA-phenyl mannosyl human serum albumin (13.6 mg/mL) and 0.3 mL of 0.5 M sodium acetate buffer (pH 5.5) was mixed and the mixture was dispensed into vials for each vial contain 1 mg protein. The vials were frozen at −70° C. and lyophilized.

Example 4

Figure 1:
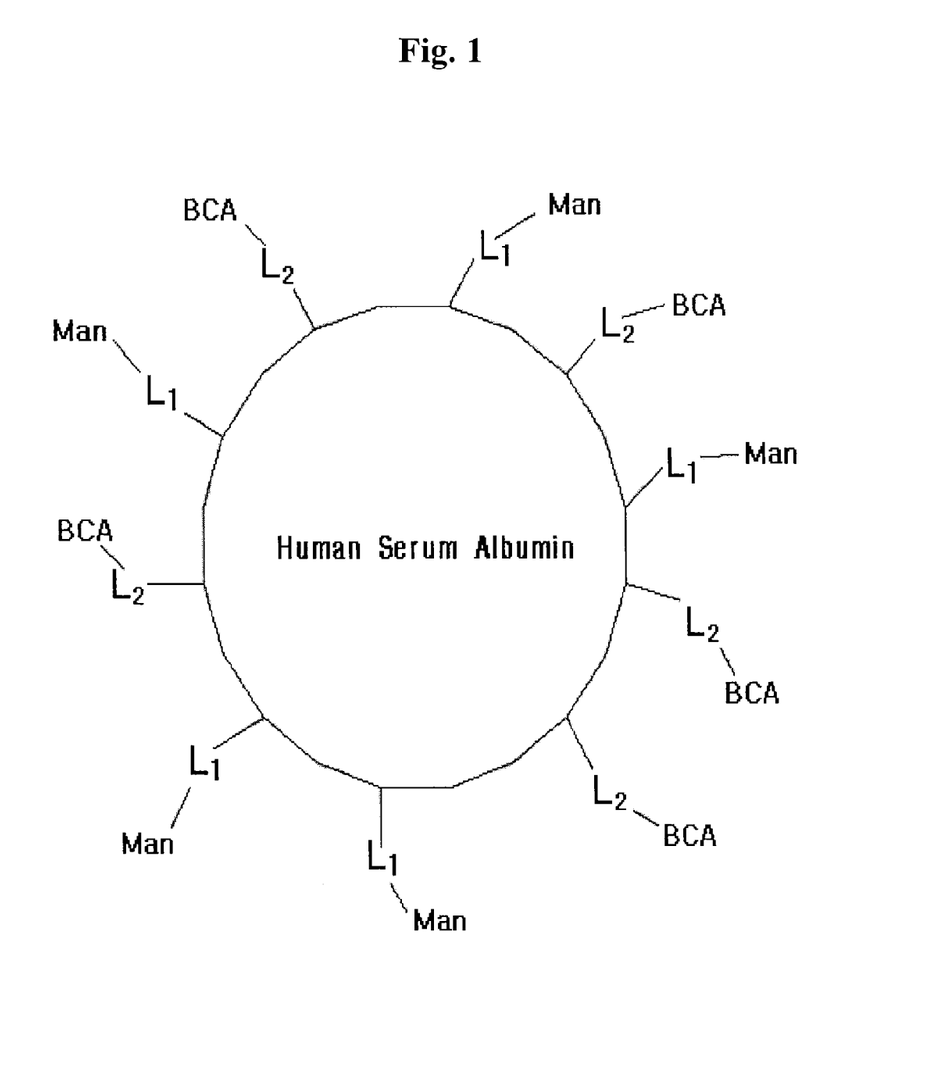
Figure 2:
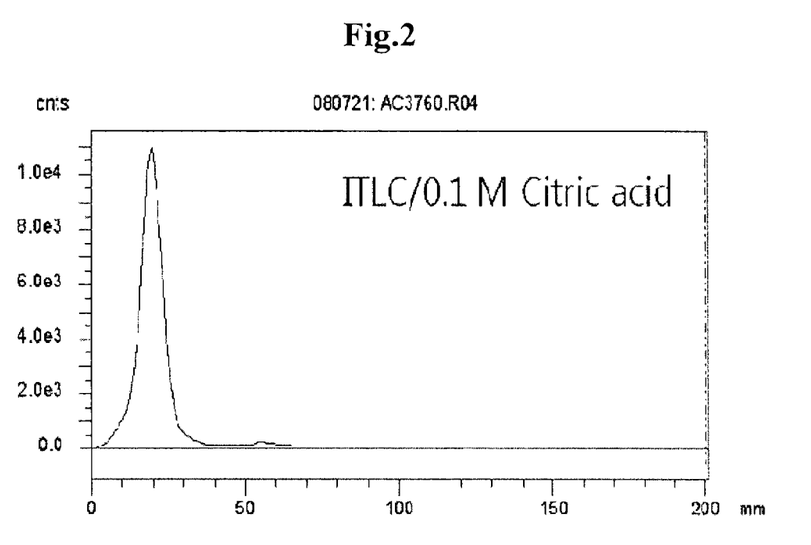
FIG. 2. $^{68}Ga$-NOTA-MSA of Example 4 analyzed by TLC.
Figure 3:
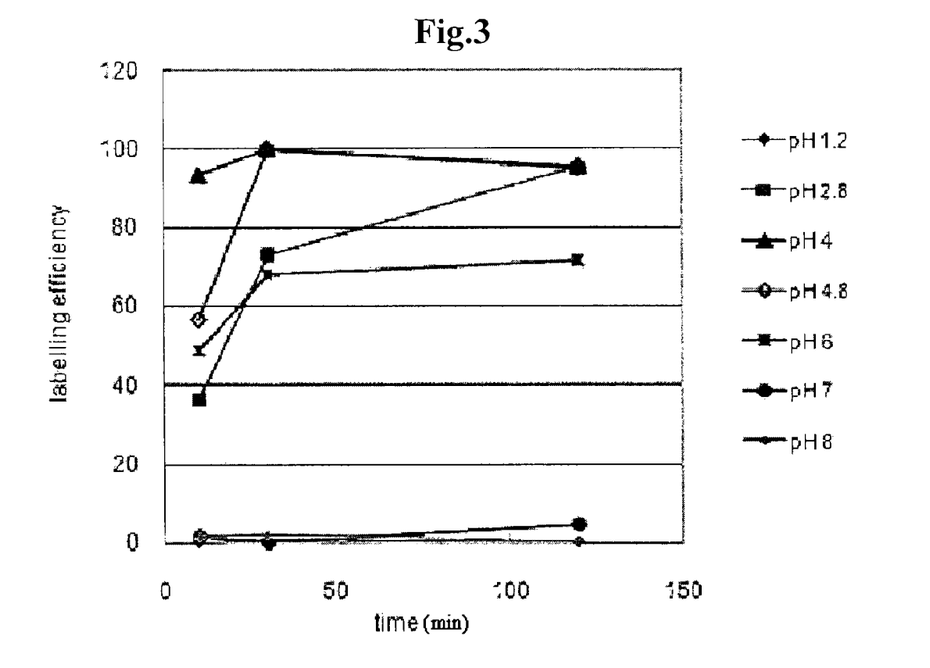
FIG. 3. NOTA-MSA of Example 2 labeled with $^{68}Ga$ in various pHs. Labeling efficiencies vs time change is plotted.

Preparation of $^{68}$Ga Labeled Agent Using a Kit for Immune Cell Imaging 1 mL of $^{68}$Ge/$^{68}$Ga-generator (Cyclotron Co., Russia) eluted $^{68}$GaCl$_3$ in 0.1 M HCl was added to a kit prepared in above Example 3. The vial was incubated at 37° C. and labeling efficiencies were checked at 10 min, 30 min, 1 hr, and 2 hr using TLC (stationary phase: TLC-SG (Gelman Co., USA), mobile phase: 0.1 M citric acid). The distribution of radioactivity in TLC plate was detected by TLC-Scanner (Bioscan Co., USA). The labeled $^{68}$Ga remained at the origin and unlabeled $^{68}$Ga moved to solvent front (FIG. 2). Reaction was completed after incubation at 37° C. at pH 4~% for 30 min (FIG. 3).

Comparative Example 1

$^{99m}$Tc-antimony Sulfur Colloid (ASC)

One mL of $^{99m}$TcO4$^-$ was added to an ASC kit (KAERI, Korea) and reacted at 50° C. for 30 min.

Comparative Example 2

$^{99m}$Tc-tin Colloid

One mL of $^{99m}$TcO4$^-$ was added to a tin colloid kit (KAERI, Korea) and reacted at room temperature for 10 min.

Comparative Example 3

$^{99m}$Tc-human Serum Albumin (HSA)

One mL of $^{99m}$TcO4$^-$ was added to a HSA kit (Daiichi Co., Japan) and reacted at room temperature for 10 min.

Comparative Example 4

$^{99m}$Tc-mannosyl Human Serum Albumin (MSA)

One mL of $^{99m}$TcO4$^-$ was added to a MSA kit prepared according to Korean Patent 10-055708 and reacted at room temperature for 10 min.

Experimental Example 1

Stability Test of the Labeled Agent

Figure 4:
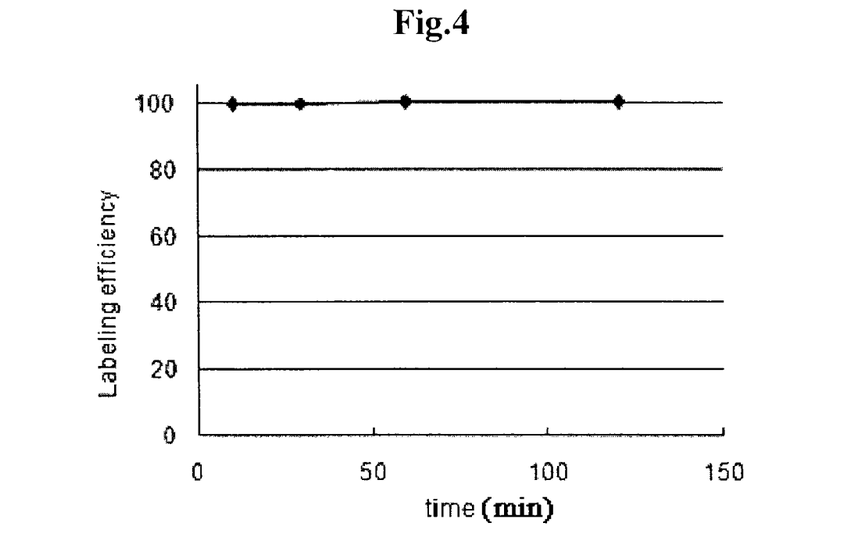
FIG. 4. Stability of $^{68}Ga$-NOTA-MSA of Example 4 investigated in human serum at 37° C.

10 μL of $^{68}$Ga-NOTA-MSA prepared according to Example 4 was mixed with 100 μL of human serum and incubated at 37° C. Radiochemical purities were checked using ITLC as described in Example 4. The results are shown at FIG. 4.

$^{68}$Ga-NOTA-MSA showed higher than 99% stability in human serum at 37° C. (FIG. 4). This stability is enough for nuclear medicine practice because most labeled agents should be injected to patients within 1 hr after preparation.

Experimental Example 2

Confirmation of Lymph Node Uptake Using Gamma Camera and PET Image

Lymph node uptakes of $^{99m}$Tc labeled agents in rats (weight 200 g, male, Sprague-Daley) were imaged using a gamma camera (Sigma 410, Ohio-Nuclear, USA). 500 μCi/10 μL of each $^{99m}$Tc labeled agent prepared as comparative examples 1, 3 and 4 was injected into rat footpad. Images were obtained after 1 hr using a gamma camera. $^{68}$Ga-NOTA-MSA (500 μCi/10 μL) prepared as Example 4 was injected into a mouse (weight 20 g, male, ICR) footpad and an image was obtained using an animal PET scanner (GE Healthcare, Princeton, USA) after 1 hr. The results are shown in FIGS. 5 and 6.

Figure 5:
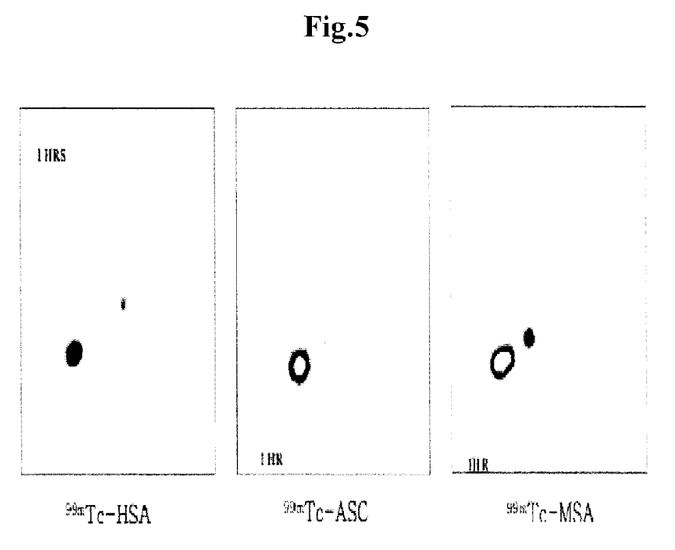
FIG. 5. Gamma camera images obtained after injection of comparative examples ($^{99m}Tc$-HSA, $^{99m}Tc$-ASC, and $^{99m}Tc$-MSA) into right footpads of rats. Radioactivities moved to lymph nodes 1 hr after injection.
Figure 6:
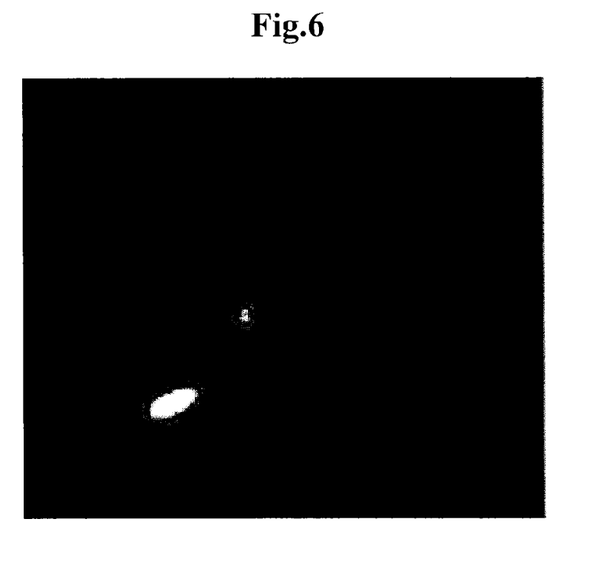
FIG. 6. PET image of $^{68}$Ga-NOTA-MSA of Example 4 showing movement of radioactivity to a lymph node 1 hr after injection into a mouse right footpad.

According to conventional technology using $^{99m}$Tc labeled agent of comparative examples 1, 3 and 4, only gamma camera images could be obtained (FIG. 5). However, the $^{68}$Ga-NOTA-MSA prepared according to present invention Example 4 enabled to obtain more advanced PET image (FIG. 6).

Experimental Example 3

Confirmation of Distribution in Immune Cells after Intravenous Injection in Mice $^{68}$Ga-NOTA-MSA (1 μCi) prepared as Example 4 was injected into mice (weight 20 g, male, ICR) through a tail vein. The mice were sacrificed and organs were obtained at 10 min, 30 min, 1 hr and 2 hr post-injection. Weight and radioactivity of each organ were measured using balance and gamma scintillation counter (Cobra III, Packard, USA). Biodistribution data were derived as percentages of injected dose per tissue weight (% ID/g) from the obtained values. The results are shown in Table 2.

TABLE 2

| Biodistribution of $^{68}$Ga-NOTA-MSA in mice after tail vein injection | | | | |
|---|---|---|---|---|
| | 10 min | 30 min | 1 hr | 2 hr |
| Blood | 0.38 ± 0.19 | 0.13 ± 0.01 | 0.15 ± 0.02 | 0.1 ± 0.06 |
| Muscle | 0.41 ± 0.05 | 0.32 ± 0.05 | 0.32 ± 0.1 | 0.28 ± 0.08 |
| Heart | 1.39 ± 0.17 | 1.13 ± 0.28 | 1.34 ± 0.23 | 0.89 ± 0.23 |
| Lung | 2.52 ± 0.17 | 2.86 ± 0.42 | 3.21 ± 0.37 | 2.04 ± 0.38 |
| Liver | 61.1 ± 3.65 | 58.6 ± 2.55 | 60.87 ± 4.75 | 59.51 ± 5.43 |
| Spleen | 19.94 ± 2.62 | 18.57 ± 2.04 | 20.88 ± 2.54 | 16.82 ± 0.97 |
| Stomach | 0.2 ± 0.04 | 0.25 ± 0.11 | 0.24 ± 0.03 | 0.26 ± 0.12 |
| Intestine | 0.26 ± 0.04 | 0.28 ± 0.04 | 0.36 ± 0.02 | 0.54 ± 0.14 |
| Kidney | 3.6 ± 0.24 | 3.25 ± 0.39 | 3.98 ± 0.17 | 3.74 ± 0.26 |
| Bone | 4.43 ± 1.22 | 4.19 ± 0.45 | 4.21 ± 0.61 | 4.33 ± 0.61 |

Liver uptake was the highest (58.6~61.1% ID/g) and spleen uptake (16.8~20.1% ID/g) was the second at all time points. Bone uptake (4.2~4.4% ID/g) was the third. We concluded that $^{68}$Ga-NOTA-MSA was taken up by the tissues containing reticuloendothelial system which contains immune cells.

Experimental Example 4

PET Imaging after Intravenous Injection into Mice

Figure 7:
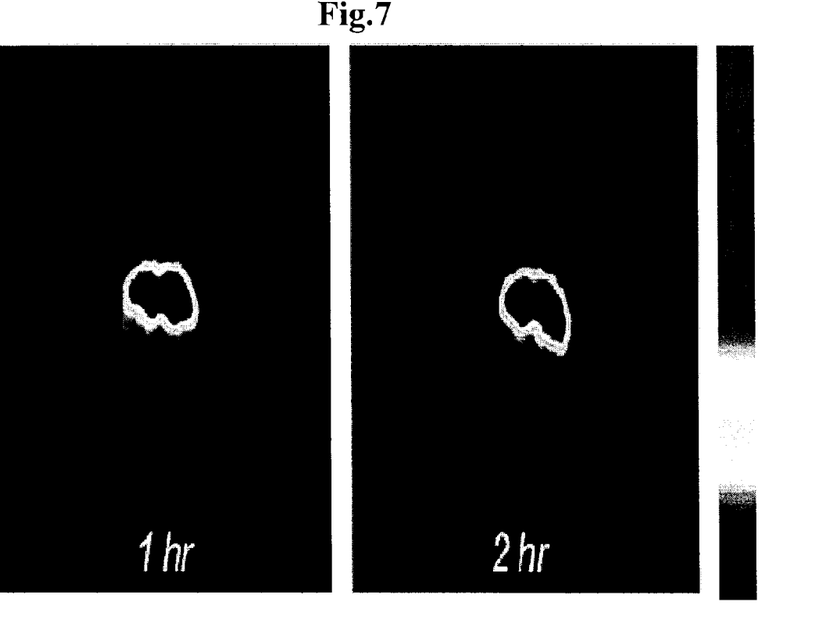
FIG. 7. PET images obtained after intravenous injection of $^{68}$Ga-NOTA-MSA of Example 4 through a tail vein of a mouse.

Each 2 mCi of $^{68}$Ga-NOTA-MSA prepared as Example 4 was injected into each mouse through a tail vein. PET images were obtained at 1 and 2 hr post-injection. Liver was the major organ showing the highest uptake and spleen was seen faintly (FIG. 7). The results represent that $^{68}$Ga-NOTA-MSA of the present invention is taken up by the reticuloendothelial system and can be applied for immune cell imaging.

The invention claimed is:

1. A sterile and apyrogenic kit of liquid, frozen or lyophilized state for preparation of a pharmaceutical composition labeled with a metallic radioisotope comprising:

(a). 10 ng~100 mg of a conjugate of the following Formula 1;

$$(Man-L_1)_n-A-(L_2-BCA)_m \quad \text{[Formula 1]}$$

wherein, Man is mannosyl group;
$L_1$ and $L_2$ are independently linker(s) or direct conjugation(s);
A is human serum albumin;
BCA is 1,4,7-triazacyclononane-1,4,7-triacetic acid (NOTA); and
m and n are independently integers from 1 to 58; and
(b). 0.01 mL~10 mL of 1 μM~10 M buffer (pH 1~9);
wherein the buffer solution is a mixture of acids selected from the group consisting of acetic acid, phosphoric acid, citric acid, fumaric acid, lactic acid, succinic acid, tartaric acid, carbonic acid, glucoheptonic acid, gluconic acid, glucuronic acid, glucaric acid and boric acid, and sodium or potassium salts thereof.

* * * * *